(12) United States Patent
Andreas et al.

(10) Patent No.: US 10,195,369 B2
(45) Date of Patent: Feb. 5, 2019

(54) PERSONALIZABLE SYSTEM AND METHOD FOR ANESTHETIZING THE TYMPANIC MEMBRANE

(71) Applicant: Tusker Medical, Inc., Menlo Park, CA (US)

(72) Inventors: Bernard H. Andreas, Los Altos, CA (US); Mansour Saleki, Cupertino, CA (US); Rohit Girotra, San Francisco, CA (US); Alfredo Cantu, Pleasanton, CA (US); Nikhil Bhat, Fremont, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 0 days.

(21) Appl. No.: 15/165,660

(22) Filed: May 26, 2016

(65) Prior Publication Data

US 2016/0375204 A1     Dec. 29, 2016

Related U.S. Application Data

(62) Division of application No. 13/551,965, filed on Jul. 18, 2012, now abandoned.
(Continued)

(51) Int. Cl.
*A61M 11/00*     (2006.01)
*A61F 11/12*     (2006.01)
(Continued)

(52) U.S. Cl.
CPC ..... *A61M 11/006* (2014.02); *A61B 17/12159* (2013.01); *A61F 11/00* (2013.01);
(Continued)

(58) Field of Classification Search
CPC ...... A61F 11/00; A61F 11/002; A61F 11/004; A61F 11/006; A61F 11/008; A61F 11/06;
(Continued)

(56) References Cited

U.S. PATENT DOCUMENTS

| 858,673 A | 7/1907 | Roswell |
| 1,920,006 A | 7/1933 | Dozier et al. |

(Continued)

FOREIGN PATENT DOCUMENTS

| CN | 86105171 A | 3/1987 |
| CN | 2087067 U | 10/1991 |

(Continued)

OTHER PUBLICATIONS

Office Action for Australian Application No. 2012287268, dated Jan. 13, 2017, 7 pages.
(Continued)

*Primary Examiner* — Kami A Bosworth

(57) ABSTRACT

Systems and methods are described for administering a solution to a tympanic membrane of an ear canal of a subject. In some embodiments, the system includes a fluid delivery channel with a proximal end, a distal end, and a lumen defined therebetween. The proximal end can include at least one of a valve and Luer connector for selectively establishing fluid communication between a solution source and the lumen of the fluid delivery channel. The distal end can include an atraumatic tip defining a plurality of spray holes for providing fluid communication between the lumen and the ear canal. The atraumatic tip can be capable of being inserted into the ear canal and positioned near the tympanic membrane with the plurality of spray holes substantially facing the tympanic membrane to fill the ear canal with the solution from a portion near the tympanic membrane out toward an outer ear portion.

17 Claims, 8 Drawing Sheets

Related U.S. Application Data

(60) Provisional application No. 61/511,270, filed on Jul. 25, 2011.

(51) Int. Cl.
    *A61M 19/00* (2006.01)
    *A61B 17/12* (2006.01)
    *A61M 31/00* (2006.01)
    *A61F 11/00* (2006.01)
    *A61F 11/08* (2006.01)

(52) U.S. Cl.
    CPC .............. *A61F 11/12* (2013.01); *A61M 19/00* (2013.01); *A61M 31/00* (2013.01); *A61F 11/004* (2013.01); *A61F 2011/085* (2013.01); *A61M 2210/0662* (2013.01)

(58) Field of Classification Search
    CPC .......... A61F 11/08; A61F 11/10; A61F 11/12; A61F 2011/085; A61M 1/0092; A61M 19/00; A61M 31/00; A61M 2039/0036; A61M 2210/0662; A61M 2210/0668; A61M 2210/0675; A61N 1/30; A61N 1/303; A61N 1/306
    See application file for complete search history.

(56) References Cited

U.S. PATENT DOCUMENTS

| | | |
|---|---|---|
| 2,458,884 A | 1/1949 | Volkmann |
| 3,741,197 A | 6/1973 | Sanz et al. |
| 3,888,958 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,149,533 A | 4/1979 | Ishikawa et al. |
| 4,206,756 A | 6/1980 | Grossan |
| 4,406,282 A | 9/1983 | Parker et al. |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,601,294 A | 7/1986 | Danby et al. |
| 4,712,537 A | 12/1987 | Pender |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,107,861 A | 4/1992 | Narboni |
| 5,135,478 A | 8/1992 | Sibalis |
| 5,160,316 A | 11/1992 | Henley |
| 5,254,081 A | 10/1993 | Maurer et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,421,818 A | 6/1995 | Arenberg |
| 5,466,939 A | 11/1995 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,674,196 A | 10/1997 | Donaldson et al. |
| D387,863 S | 12/1997 | Herman et al. |
| 5,707,383 A | 1/1998 | Bays et al. |
| 5,792,100 A | 8/1998 | Shantha |
| 5,804,957 A | 9/1998 | Coln |
| 5,827,295 A | 10/1998 | Del Rio et al. |
| 5,893,828 A | 4/1999 | Uram |
| 5,979,072 A | 11/1999 | Collins, II |
| D418,223 S | 12/1999 | Phipps et al. |
| D420,741 S | 2/2000 | Croley |
| 6,045,578 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,137,889 A | 10/2000 | Shennib et al. |
| 6,148,821 A | 11/2000 | Falco et al. |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,251,121 B1 | 6/2001 | Saadat |
| 6,295,469 B1 | 9/2001 | Linkwitz et al. |
| D450,843 S | 11/2001 | McGuckin, Jr. et al. |
| 6,347,246 B1 | 2/2002 | Perrault et al. |
| 6,358,231 B1 | 3/2002 | Schindler et al. |
| 6,440,102 B1 | 8/2002 | Arenberg et al. |
| 6,475,138 B1 | 11/2002 | Schechter et al. |
| 6,512,950 B2 | 1/2003 | Li et al. |
| 6,514,761 B1 | 2/2003 | Randall et al. |
| 6,520,939 B2 | 2/2003 | Lafontaine |
| 6,522,827 B1 | 2/2003 | Loeb et al. |
| 6,553,253 B1 | 4/2003 | Chang |
| 6,640,121 B1 | 10/2003 | Telischi et al. |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 7,123,957 B2 | 10/2006 | Avrahami |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| 8,052,693 B2 | 11/2011 | Shahoian |
| 8,192,420 B2 | 6/2012 | Morriss et al. |
| 8,249,700 B2 | 8/2012 | Clifford et al. |
| 8,409,175 B2 | 4/2013 | Lee et al. |
| 8,425,488 B2 | 4/2013 | Clifford et al. |
| 8,452,392 B2 | 5/2013 | Morriss et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 9,011,363 B2 | 4/2015 | Clopp et al. |
| 9,023,059 B2 | 5/2015 | Loushin et al. |
| 9,216,112 B2 | 12/2015 | Clifford et al. |
| 9,364,648 B2 | 6/2016 | Girotra et al. |
| 9,387,124 B2 | 7/2016 | Clifford |
| 9,392,229 B2 | 7/2016 | Morriss et al. |
| 9,833,601 B2 | 12/2017 | Clifford |
| 9,950,157 B2 | 4/2018 | Morriss et al. |
| 2002/0026125 A1 | 2/2002 | Leysieffer |
| 2002/0069883 A1 | 6/2002 | Hirchenbain |
| 2002/0111585 A1 | 8/2002 | Lafontaine |
| 2002/0138091 A1 | 9/2002 | Pflueger |
| 2002/0161379 A1 | 10/2002 | Kaplan et al. |
| 2002/0169456 A1 | 11/2002 | Tu et al. |
| 2003/0018291 A1 | 1/2003 | Hill et al. |
| 2003/0060799 A1 | 3/2003 | Arenberg et al. |
| 2003/0093057 A1 | 5/2003 | Zhang et al. |
| 2003/0199791 A1 | 10/2003 | Boecker et al. |
| 2004/0054339 A1 | 3/2004 | Ciok et al. |
| 2005/0094835 A1 | 5/2005 | Doty |
| 2005/0154357 A1* | 7/2005 | Pinel .................... A61J 9/00 604/247 |
| 2005/0182385 A1 | 8/2005 | Epley |

(56) References Cited

U.S. PATENT DOCUMENTS

| | | |
|---|---|---|
| 2005/0235422 A1 | 10/2005 | Wallace |
| 2005/0240147 A1 | 10/2005 | Makower et al. |
| 2006/0142700 A1 | 6/2006 | Sobelman et al. |
| 2006/0155304 A1 | 7/2006 | Kaplan et al. |
| 2006/0177080 A1 | 8/2006 | Smith |
| 2007/0003096 A1 | 1/2007 | Nam |
| 2007/0078372 A1 | 4/2007 | Reddy et al. |
| 2007/0183613 A1 | 8/2007 | Juneau et al. |
| 2007/0233222 A1 | 10/2007 | Roeder et al. |
| 2008/0011308 A1 | 1/2008 | Fleming |
| 2008/0051804 A1 | 2/2008 | Cottler et al. |
| 2008/0058756 A1 | 3/2008 | Smith |
| 2008/0065002 A1* | 3/2008 | Lobl ............... A61M 25/0068 604/21 |
| 2008/0107287 A1 | 5/2008 | Beard |
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163848 A1 | 6/2009 | Morriss et al. |
| 2009/0209972 A1 | 8/2009 | Loushin et al. |
| 2009/0262510 A1 | 10/2009 | Pekkarinen et al. |
| 2009/0270807 A1 | 10/2009 | Mas et al. |
| 2009/0299344 A1 | 12/2009 | Lee et al. |
| 2010/0030131 A1 | 2/2010 | Morriss et al. |
| 2010/0041447 A1 | 2/2010 | Graylin |
| 2010/0061581 A1 | 3/2010 | Soetejo et al. |
| 2010/0198135 A1 | 8/2010 | Morriss et al. |
| 2010/0300460 A1 | 12/2010 | Falco et al. |
| 2011/0001564 A1 | 1/2011 | Hori |
| 2011/0015645 A1 | 1/2011 | Liu et al. |
| 2011/0048414 A1 | 3/2011 | Hoekman et al. |
| 2011/0268303 A1 | 11/2011 | Ahsani |
| 2011/0288559 A1 | 11/2011 | Shahoian |
| 2012/0310145 A1 | 12/2012 | Clifford et al. |
| 2013/0090544 A1 | 4/2013 | Clifford et al. |
| 2013/0190678 A1 | 7/2013 | Andreas et al. |
| 2013/0197426 A1 | 8/2013 | Morriss et al. |
| 2013/0223702 A1 | 8/2013 | Holsing et al. |
| 2014/0102461 A1 | 4/2014 | Girotra et al. |
| 2014/0194891 A1 | 7/2014 | Shahoian |
| 2014/0276352 A1 | 9/2014 | Kermani et al. |
| 2014/0276906 A1 | 9/2014 | Andreas et al. |
| 2015/0068539 A1 | 3/2015 | Morriss et al. |
| 2016/0361204 A1 | 12/2016 | Girotra et al. |
| 2017/0014272 A1 | 1/2017 | Ray et al. |
| 2017/0028193 A1 | 2/2017 | Morriss et al. |
| 2018/0085563 A1 | 3/2018 | Clifford et al. |

FOREIGN PATENT DOCUMENTS

| | | |
|---|---|---|
| CN | 2409940 Y | 12/2000 |
| DE | 19618585 | 11/1997 |
| EP | 0214527 A1 | 3/1987 |
| FR | 2526656 | 11/1983 |
| JP | S59-129815 | 8/1984 |
| JP | H 07-116190 A | 5/1995 |
| JP | 2010-524584 | 7/2010 |
| WO | WO 92/10223 | 6/1992 |
| WO | WO 2002/043795 | 6/2002 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2009/105619 | 8/2009 |
| WO | WO 2010/014894 | 2/2010 |
| WO | WO 2011/081772 | 7/2011 |
| WO | WO 2013/016098 | 1/2013 |
| WO | WO 2013/181009 | 12/2013 |
| WO | WO 2014/158543 | 10/2014 |
| WO | WO 2017/011777 | 1/2017 |

OTHER PUBLICATIONS

Office Action for European Application No. 12743007.2, dated Jun. 12, 2017, 4 pages.
Office Action for Mexican Application No. MX/a/2014/001073, dated May 9, 2016, 3 pages.
International Search Report and Written Opinion for International Application No. PCT/US2016/042577, dated Dec. 6, 2016, 14 pages.
U.S. Appl. No. 60/912,902, filed Apr. 19, 2007.
Patent Examination Report No. 1 for Australian Patent Application No. 2008242735, dated Aug. 8, 2012, 3 pages.
Patent Examination Report No. 1 for Australian Patent Application No. 2013209354, dated Oct. 13, 2014, 5 pages.
First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 3 pages.
Office Action for European Application No. 08746237.0, dated Mar. 24, 2016, 3 pages.
Office Action for European Application No. 08746237.0, dated Aug. 4, 2015, 7 pages.
Supplementary Partial Search Report for European Application No. 08746237.0, dated Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
International Search Report for International Application No. PCT/US2008/060779, dated Sep. 3, 2008.
Written Opinion for International Application No. PCT/US2008/060779, dated Sep. 3, 2008.
Office Action for U.S. Appl. No. 11/749,733, dated Jun. 10, 2009, 13 pages.
Office Action for U.S. Appl. No. 11/749,733, dated Dec. 2, 2008, 9 pages.
U.S. Appl. No. 61/085,360, filed Jul. 31, 2008.
Patent Examination Report No. 1 for Australian Application No. 2009276384, dated Apr. 14, 2014, 3 pages.
Office Action for Canadian Application No. 2,732,595, dated Dec. 8, 2015, 4 pages.
Office Action for Russian Application No. 2011-07228, dated May 24, 2013.
International Search Report for International Application No. PCT/US2009/052395, dated Nov. 6, 2009.
Written Opinion for International Application No. PCT/US2009/052395, dated Nov. 6, 2009.
Patent Examination Report No. 1 for Australian Application No. 2010337214, dated Feb. 27, 2015, 3 pages.
Office Action for Chinese Application No. 201080065012.2, dated Mar. 31, 2016, 20 pages.
International Search Report for International Application No. PCT/US2010/058718, dated Feb. 17, 2011.
Written Opinion for International Application No. PCT/US2010/058718, dated Feb. 17, 2011.
International Search Report for International Application No. PCT/US2010/042128, dated Aug. 27, 2010.
Office Action for Australian Application No. 2012287268, dated Feb. 11, 2016.
Office Action for European Application No. 12743007.2, dated Jul. 21, 2016, 5 pages.
Notification of Reasons for Refusal for Japanese Application No. 2014-522882, dated May 31, 2016.
Office Action for U.S. Appl. No. 13/551,965, dated Sep. 10, 2015, 10 pages.
Office Action for U.S. Appl. No. 13/551,965, dated Feb. 26, 2016, 10 pages.
International Search Report for International Application No. PCT/US2012/047179, dated Mar. 11, 2013.

(56) References Cited

OTHER PUBLICATIONS

Written Opinion for International Application No. PCT/US2012/047179, dated Mar. 11, 2013.
First Office Action for Chinese Patent Application No. 201380027926.3, dated May 3, 2016.
International Search Report for International Application No. PCT/US2013/041816, dated Sep. 16, 2013, 7 pages.
Written Opinion for International Application No. PCT/US2013/041816, dated Sep. 16, 2013, 7 pages.
International Search Report and Written Opinion for International Application No. PCT/US2014/018017, dated May 22, 2014, 12 pages.
International Search Report for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
Examination Report No. 1 for Australian Application No. 2017200513, dated Sep. 27, 2017, 4 pages.
Office Action for Canadian Application No. 2,843,147, dated May 31, 2018, 3 pages.

\* cited by examiner

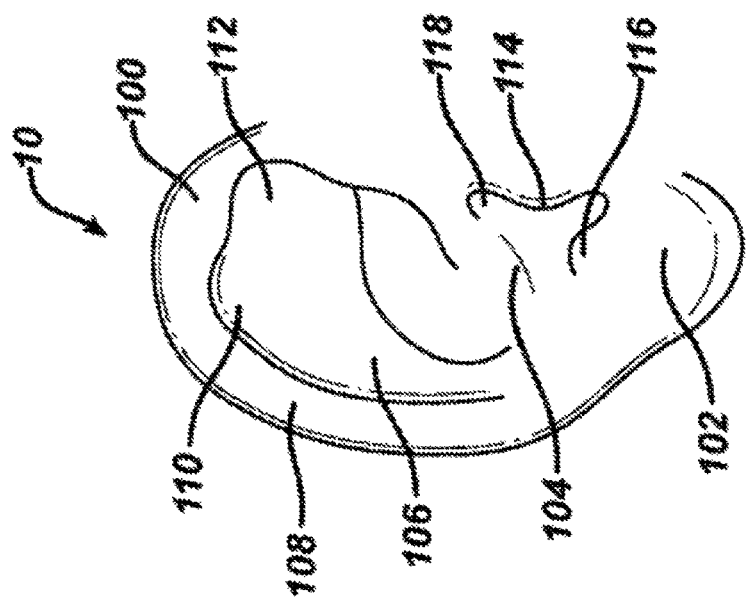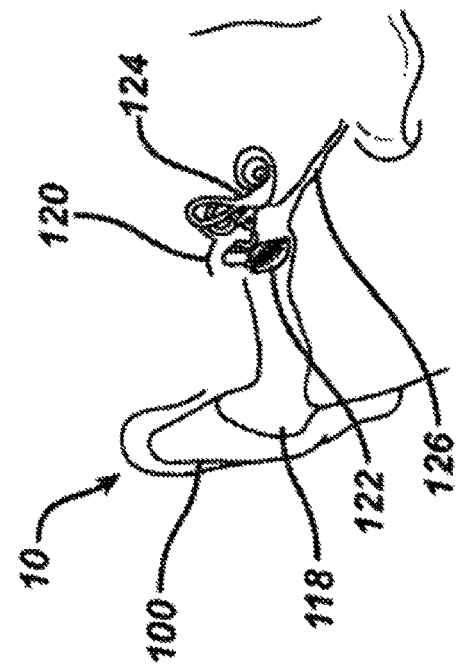

PERSONALIZABLE SYSTEM AND METHOD FOR ANESTHETIZING THE TYMPANIC MEMBRANE

CROSS-REFERENCE TO RELATED APPLICATIONS

This application is a divisional of and claims priority to U.S. patent application Ser. No. 13/551,965, filed Jul. 18, 2012, entitled "Personalizable System and Method for Anesthetizing the Tympanic Membrane," which claims the benefit of and priority to U.S. Provisional Patent Application No. 61/511,270, filed Jul. 25, 2011, entitled "Personalizable System and Method for Anesthetizing the Tympanic Membrane," the contents of each of which are incorporated herein by reference in their entirety.

TECHNICAL FIELD

The present invention is generally related to medical devices and methods and, in particular, to devices and methods for filling and retaining fluid drug in the ear canal of a human patient.

BACKGROUND

The present invention provides systems and methods useful for anesthetizing the tympanic membrane and/or the ear canal of a patient in preparation for a surgical procedure, including the placement of a tympanostomy tube (or pressure equalization tube) across a tympanic membrane of an ear. Additionally, the invention provides systems and methods for administering and retaining fluid in the ear canal of a human patient for treatment of the ear canal and/or the tympanic membrane.

Otitis media is among the most common diagnoses made by pediatricians. A majority of children may have at least one episode of otitis media ("ear infection") prior to their third birthday. Otitis media is often caused by an inability of the Eustachian tube to drain fluid from the middle ear. Otitis media is often treated with antibiotics.

A significant number of children exhibit recurrent episodes of otitis media and/or otitis media with effusion. Treatment of these more severe cases often involves the placement of a tympanostomy tube across the tympanic membrane to provide adequate drainage and/or ventilation of the middle ear and reduce the likelihood of future infections. Tympanostomy tubes provide fluid communication between the middle and outer ear (e.g., pressure equalization) and typically fall out spontaneously within about a year of placement. Tympanostomy tube placement is among the most frequent surgical procedures performed in the pediatric population. It has been estimated that more than a million tympanostomy tubes may be placed each year, with typical patients being between about 18 months and 7 years of age at the time of the procedure.

Tympanostomy tube placement is typically performed in an out-patient surgery setting under general anesthesia. After administering the general anesthesia, the physician typically first examines the external auditory canal and tympanic membrane under microscopic visualization through a handheld conical shaped speculum. The physician then makes an incision in the tympanic membrane (a "myringotomy"), typically using a standard, small profile scalpel which the physician advances through the conical speculum. The physician may then pass a suction device through the myringotomy into the middle ear, to aspirate fluid/effusion from the middle ear. The physician will then place the tympanostomy tube across the tympanic membrane, typically using a basic tool, such as forceps, for holding and advancing the tube into the myringotomy.

Systems and methods have been proposed for deploying tympanostomy tubes without having to use general anesthesia. Such systems are described for example in U.S. Patent Application Publication No. 2011/001564 ("Tympanic Membrane Pressure Equalization Tube Delivery System"), U.S. Patent Application Publication No. 2010/0198135 ("Systems and Methods for Anesthetizing Ear Tissue"), U.S. Patent Application Publication No. 2009/0163848 ("Iontophoresis Methods"), and U.S. Patent Application Publication No. 2009/0262510 ("Disposable Iontophoresis System and Tympanic Membrane Pain Inhibition Method"), each of which is incorporated by reference in their entirety. These publications describe integrated methods for delivering tympanostomy tubes and appropriate anesthesia, but do not describe how to personalize these systems for a particular patient, so that delivery of a tympanostomy tube can be achieved with minimal discomfort to the patient.

In light of the above, it would be desirable to provide improved devices, systems, and methods for delivering an anesthetizing solution into the ear canal. Such systems and methods would also be useful for administering other therapeutic solutions to the ear canal and tympanic membrane. It would generally be beneficial if these improvements facilitated tympanostomy tube placement without requiring multiple devices and operator-performed steps. At least some of these advantages may be provided by the embodiments described herein.

SUMMARY

The present invention provides systems and methods for administering a therapeutic solution to the ear canal and/or for anesthetizing a tympanic membrane of an ear for surgical procedures such as placing a tympanostomy tube (or pressure equalization tube) across the tympanic membrane. The systems are personalizable to ensure proper anesthetizing solution and/or therapeutic solution administration.

In one aspect, the invention is directed to a method for administering a therapeutic solution to the ear canal of a patient. The method includes selecting or adjusting a headset based on a size and shape of the patient's head, positioning the headset about the patient's head and filling the ear canal with the therapeutic solution. An ear plug is inserted into the ear canal either prior to or following filling the ear canal.

In one embodiment, the method further includes selecting an ear plug based on a size and shape of the ear canal and positioning the selected ear plug onto the headset. In another embodiment, the method includes inserting the ear plug into the patient's ears prior to filling the ear canal with the therapeutic solution. In still another embodiment, the method includes inserting the ear plug into the patient's ear following filling the ear canal with the therapeutic solution. In yet another embodiment, the therapeutic solution may be administered to a second ear canal either simultaneously or sequentially. In a further embodiment, the headset comprises a first fill system valve through which the solution is administered to a first ear canal; and in another embodiment, the headset comprises a second fill system valve through which the solution is administered to a second ear canal. In a further embodiment, the solution is administered using a manual fill nozzle and in another, the therapeutic solution is retained in the ear canal throughout a predetermined treatment period. In another embodiment the method further includes removing the solution from the ear canal following the predetermined treatment period.

In another aspect, the invention is directed to a device for administering a therapeutic solution to the ear canal of a patient. The device includes a headset having a headset frame that is designed to conform to the size and shape of the patient's head and an ear plug that is designed to conform to the size and shape of the patient's ear canal.

In one embodiment of the device, the headset further comprises a fill system for filling the ear canal with the therapeutic solution. In another embodiment, the fill system includes a valve for attachment to a therapeutic solution delivery device, the valve being fluidly connected to a spray tip. In a further embodiment, the fill system includes a second valve, the second valve being fluidly connected to a second spray tip. In yet another embodiment, the headset includes locking arms, the locking arms having a first position and a second position, the first position permitting visualization of the ear canal, and the second position providing for sealing of the ear canal by the ear plug. In still another embodiment, the ear plugs further include a venting system selected from the group consisting of vent holes, vent slits and vent screens.

In a further aspect, the invention is directed to a method for administering a therapeutic solution to the ear canal of a patient and for delivering the solution to the tympanic membrane using iontophoresis. The method includes selecting or adjusting a headset based on a size and shape of the patient's head, the headset including an iontophoresis electrode connected to a control unit and a return electrode, positioning the headset about the patient's head, filling the ear canal with the therapeutic solution, attaching the return electrode to the patient and activating a control unit to initiate an iontophoresis procedure. The ear plug is inserted into the ear canal either prior to or following filling the ear canal.

In one embodiment, the method includes selecting an ear plug based on a size and shape of the ear canal and positioning the selected ear plug onto the headset. In another embodiment, the method includes inserting the ear plug into the patient's ears prior to filling the ear canal with the therapeutic solution where the iontophoresis electrode establishes electrical connection with the therapeutic solution during filling of the ear canal. In yet another embodiment, the ear plug is inserted into the patients ears following filling the ear canal with the therapeutic solution where the iontophoresis electrode establishes electrical connection with the therapeutic solution and in another, the therapeutic solution may be administered to a second ear canal either simultaneously or sequentially. In a further embodiment, the headset includes a first fill system valve through which the solution is administered to a first ear canal; and in another embodiment, the headset includes a second fill system valve through which solution is administered to a second ear canal. In a further embodiment, the substance is administered using a manual fill nozzle and in another, the therapeutic solution is retained in the ear canal throughout a predetermined treatment period. In yet another embodiment, the solution is removed from the ear canal following the predetermined treatment period.

In another aspect, the invention is directed to a device for administering a therapeutic solution to the ear canal of a patient and for iontophoresis delivery to the tympanic membrane. The device includes a headset having a headset frame that is designed to conform to the size and shape of the patient's head and an iontophoresis electrode that is connected to a control unit and a return electrode for delivering the solution into the tympanic membrane, and an ear plug that is designed to conform to the size and shape of the patient's ear canal.

In one embodiment, the headset further includes a fill system for filling the ear canal with the therapeutic solution. In another embodiment, the fill system includes a valve for attachment to a therapeutic solution delivery device, the valve being fluidly connected to a spray tip. In a further embodiment, the fill system includes a second valve, the second valve being fluidly connected to a second spray tip. In still another embodiment, the headset includes locking arms, the locking arms having a first position and a second position, the first position permitting visualization of the ear canal and the second position provides for sealing of the ear canal by the ear plug. In yet another embodiment the ear plugs further include a venting system selected from the group consisting of vent holes, vent slits and vent screens.

In a further aspect, the invention is directed to a method for anesthetizing a tympanic membrane of a human patient. The method involves inserting an ear plug sizer into a patient's ear canal to determine the appropriate ear plug size, and positioning the ear plug onto a headset. The headset is then positioned about the patient's head. The ear canal is filled with an anesthetizing solution and the ear plug of the headset is inserted into the patient's ear. The control unit is activated to begin the iontophoresis procedure.

In one embodiment, the method includes preparing the anesthetizing solution and warming it to body temperature. In a further embodiment the method of the invention includes filling the headset by injecting the solution into a fluid delivery channel of the headset until the solution exits the ear plugs. In yet another embodiment, the method of the invention includes removing air from the fluid delivery channel. The removal of air may be accomplished using a dual chamber instillation port, or by incorporating a semi-porous material into the fluid delivery channel.

In another aspect, the invention is directed to a method for filling and retaining fluid in the ear canal of a human patient. The method includes inserting an ear plug sizer into a patient's ear canal to determine the appropriate ear plug size and selecting an ear plug based on the determined appropriate ear plug size. The method further includes positioning the selected ear plug onto a headset, positioning the headset about the patient's head, and inserting the ear plug of the headset into the patient's ear for retaining said fluid in the patient's ear canal. The ear canal is filled with the fluid during the method for filling and retaining fluid in the patient's ear canal.

In a second aspect, the invention is directed to a system for anesthetizing a tympanic membrane of a human patient. The system includes ear plug sizers, iontophoresis electrodes, and ear plugs sized by said ear plug sizers for fluidly sealing an ear canal of the patient. The ear plugs are positioned about the iontophoresis electrodes. The system further includes a control unit and a headset. The headset includes a headset frame that fluidly connects the iontophoresis electrodes to a source of anesthetizing solution, and electrically connects the two electrodes to the control unit.

In one embodiment, the system includes temporal pads attached at the ends of the headset frame. In another embodiment, the system includes a wire support frame to support the ear plug in the x, y, and z directions. In a further embodiment, the headset frame is sized according to the size of the patient's head. In yet another embodiment, the headset frame includes accessories useful for watching and/or listening to movies, music or video games or attachments such as horns, antlers, antennas and elephant ears. In another embodiment, the anesthetizing solution includes lidocaine, lidocaine plus epinephrine or lidocaine, epinephrine and sodium bicarbonate.

In another aspect, the invention is directed to a headset for use in anesthetizing a tympanic membrane of a human patient. The headset includes a headset frame with a first headset arm and a second headset arm. The first headset arm includes a first iontophoresis electrode and a first fill system tip and the second headset arm includes a second iontophoresis electrode and a second fill system tip. The headset frame fluidly connects the iontophoresis electrodes and the fill system tips to a source of anesthetizing solution. The fill system tip has an atraumatic tip and at least one spray hole for delivering the anesthetizing solution to the tympanic membrane.

In one embodiment, the fill system tips comprise three spray holes spaced 120 degrees apart.

In a further aspect, the invention is directed to a headset for use in administering a solution into the ear canal of a human patient and retaining the solution in the ear canal. The headset has a headset frame with a first headset arm having a first fill system tip and a first earplug, and a second headset arm having a second fill system tip and a second earplug. The headset frame fluidly connects the fill system tips to a source of solution and the fill system tip has an atraumatic tip and spray holes for delivering the solution to the ear canal. The ear plugs retain the solution in the ear.

In one embodiment, the solution is selected from the group consisting of an anesthetizing solution, an antibacterial solution, an antifungal solution, an anti-inflammatory solution or a ceruminolytic solution.

In another aspect, the invention is directed to a device for administering a solution into the ear canal of a human patient. The device has a distal end with an atraumatic tip and at least one spray hole, a proximal end with a luer connector for attachment to a source of solution and a lumen between the proximal end and the distal end. The lumen has a bend angle of between about 0 and 140 degrees.

In one embodiment, the lumen has a bend angle of between about 120 and 140 degrees. In another embodiment, a speculum is fixedly attached to the device. In still another embodiment, the solution is selected from the group consisting of an anesthetizing solution, an antibacterial solution, an antifungal solution, an anti-inflammatory solution or a ceruminolytic solution.

In another aspect, the invention is an ear plug sizer kit for determining the appropriate ear plug for use in a human patient. The kit includes a first ear plug sizer having a first lug with a first outer diameter and a first ear plug with a first sealing diameter. The first lug is fixedly connected to a first end of a first shaft and the first ear plug is detachably connected to a second end of the first shaft. The kit further includes a second ear plug sizer having a second lug with a second outer diameter and a second ear plug with a second sealing diameter. The second lug is fixedly connected to a first end of a second shaft and the second ear plug is detachably connected to a second end of the second shaft. The first outer diameter is equivalent to the first sealing diameter and the second outer diameter is equivalent to the second sealing diameter.

In another aspect, the invention is a method for filling a patient's ear canal with a therapeutic solution while minimizing air bubbles in the ear canal. The method includes sealing the ear canal with an ear plug such that there is minimal leakage of the therapeutic solution from the ear canal, providing ear canal vents for venting air from within the ear canal, and turbulently filling the ear canal by administering the therapeutic solution through one or more spray holes in a fill system while venting the ear canal as a result of low pressure escape of air through the ear canal vents.

In one embodiment, the ear canal vents comprise ear plug vent holes and in another embodiment, the ear canal maintains a maximum pressure in the ear canal of 25 kilopascals.

In yet another aspect, the invention is a device for filling a patient's ear canal with a therapeutic solution while minimizing air bubbles in a patient's ear canal. The device includes an ear plug that is designed to conform to the size and shape of the patient's ear canal to seal the ear canal from leakage of the therapeutic solution, a fill system including an atraumatic tip portion and one or more spray holes to turbulently fill the ear canal with the therapeutic solution, and a vent system that is designed to maintain a maximum pressure in the ear canal at or below 25 kilopascals.

In one embodiment, the vent system comprises ear plug vent holes. In another embodiment, the fill system comprises three or more spray holes.

For a further understanding of the nature and advantages of the invention, reference should be made to the following description taken in conjunction with the accompanying figures. However, each of the figures is provided for the purpose of illustration and description only and is not intended to limit the scope of the embodiments of the present invention.

BRIEF DESCRIPTION OF THE DRAWINGS

FIG. 1A shows a frontal view of an outer ear.

FIG. 1B shows a partial cross-sectional view of an outer, middle and inner ear.

DETAILED DESCRIPTION

Figure 2:
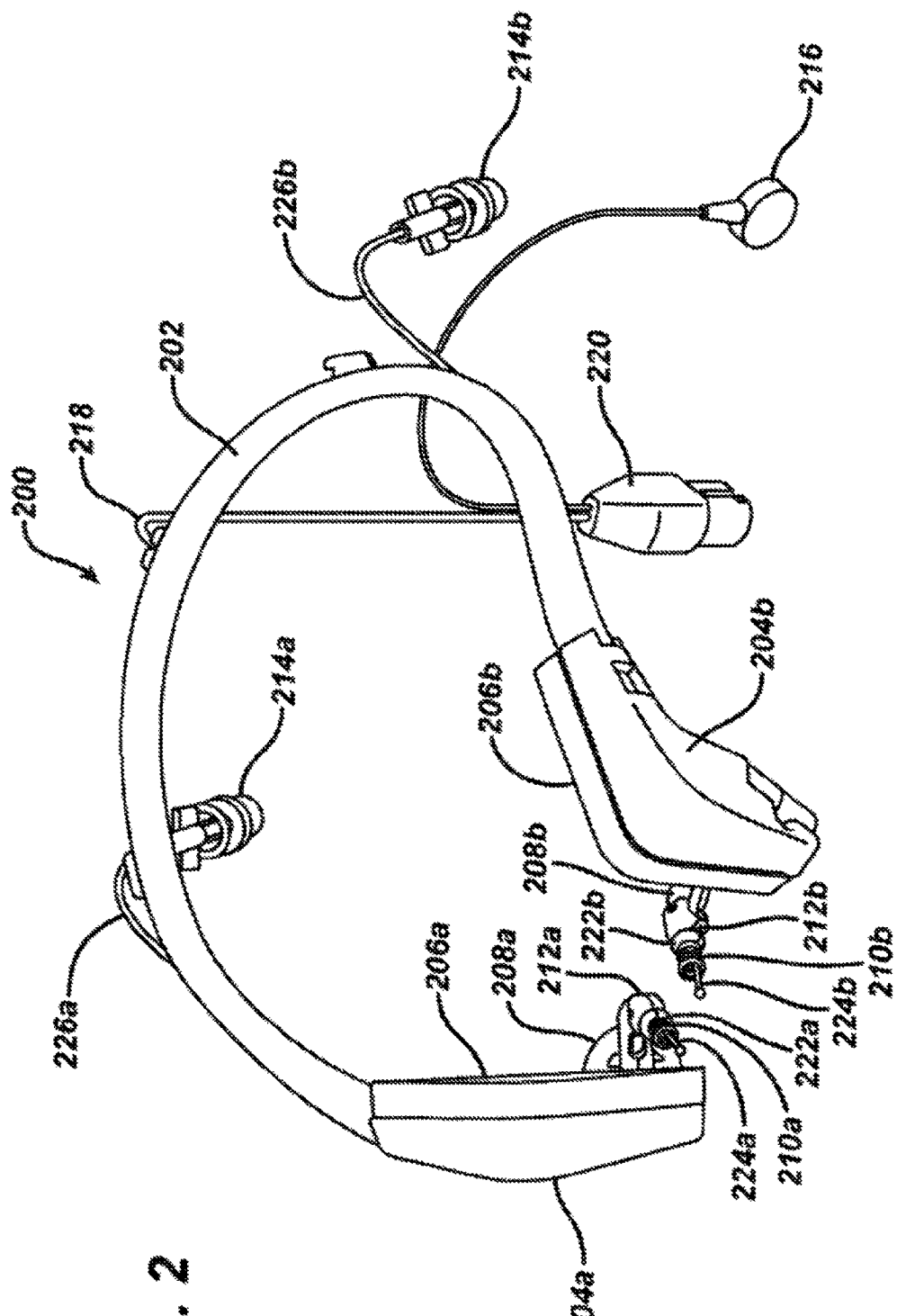
FIG. 2 shows a perspective view of a headset for iontophoretic substance delivery, according to one embodiment of the invention.

The embodiments of the invention are intended to provide systems that are useful for delivering and retaining a drug solution in a patient's ear canal that are individually and uniquely adapted to be used for a particular patient. In this way, variations in patient anatomy can be accommodated while maintaining patient comfort. Further, efficient filling of the ear canal can be accomplished under direct visualization with a microscope, limiting the amount of air bubbles in the ear canal, and facilitating the venting of excess air or fluid.

FIG. 1A shows a view of an outer ear 10. The outer ear 10 includes a major element known as the auricle 100. The outer ear serves as a funnel for directing sounds into the internal portions of the ear. The major physical features of the ear include the lobule, 102, concha 104, anthelix 106, helix 108, scapha 110, triangular fossa 112, tragus 114, antitragus 116 and ear canal 118.

FIG. 1B shows a cross-section of the inner and outer portions of the ear. The outer ear 10 is shown connected to the ear canal 118. The ear canal is shown as a relatively straight passage, but is often a more curved, tortuous passageway. The ear canal is connected to the middle ear 120, which includes the tympanic membrane 122. The middle ear 120 in turn is connected to the internal ear 124 which leads to the auditory tube 126 (also known as the Eustachian tube). The middle ear 120 normally has a pocket of air behind the tympanic membrane 122. When the middle ear 120 is infected, fluid swells behind the tympanic membrane 122. Fluid expansion causes extreme pain to an individual with a middle ear infection, as often occurs in young children.

As can be imagined from FIGS. 1A and 1B, the anatomies of the ear canal 118 and the tympanic membrane 122 are quite variable across individuals of different ages, and even among those of the same age. The length and diameter of the ear canal 118 may vary, as well as its shape. Further, the size and position of the tympanic membrane 122 is not constant. Accordingly, it would be useful for treatment of middle ear infection, to be able to individualize the systems that are used to perform procedures in the ear.

FIG. 2 shows a headset 200 according to one embodiment of the invention. The headset 200 includes a headset frame 202, dual temporal pads 204a and 204b, temporal cushions 206a and 206b, locking arms 208a and 208b, electrodes 210a and 210b, locking arm elbows 212a and 212b, fill system valves 214a and 214b, fill system tips 224a and 224b, fill system tubing 226a and 226b, a return electrode connector 216, the electrode wiring 218 and the control unit connector 220.

The headset 200 is useful for administering an iontophoretic substance to the ear canal and retaining it in the ear canal for anesthetizing the ear canal and tympanic membrane prior to treatment. The frame 202 serves to connect the portions of the headset together. These portions extend from the right side to the left side of the head and extend to the temporal pads 204a and 204b on the right and left side, respectively. The frame 202 is thus configured to be placed around or over a patient's head. Further, the frame 202 secures the headset 200 on the patient's head. In this way, the frame 202 is sized appropriately for the patient such that when in position over the patient's ears, the frame supplies a compressive force to the patient's head. A sizing aid may be used to determine the appropriate headset size. In some embodiments, the frames come in 3 sizes, small, medium and large, and in other embodiments, they may come in 2, 4, 5, 6 or more sizes. Further, in another embodiment, the frame may be expandable such that a single size may be supplied that can be adjusted according to the size of the patient's head. In other embodiments, accessories may be attached to the frame base to entertain a patient during the iontophoresis procedure. These accessories include, but are not limited to be re-usable glasses that can stream movies, music, and/or video games, fun attachments such as horns, antler, antennas, elephant ears, etc. Bone conduction could also be included such that a sound vibration element may be incorporated into the headset to entertain and/or distract a patient.

In a further aspect, the headset 200 may be useful for administering a drug solution or other therapeutic solution to the ear canal and retaining the solution in the ear canal for treating the ear canal or the tympanic membrane or for anesthetizing the ear canal or tympanic membrane. The electrodes, return electrode connector, electrode wiring and control unit connector would not be present in such system. Such solutions include but are not limited to antifungal or antibacterial agents such as benzalkonium chloride, boric acid, acetic acid, and clotrimazole, anti-inflammatory agents such as beclamethazone and antibiotic and steroids such as betnesol, prednisolone sodium phosphate, gentamycin, neomycin, and quinolones, astringent agents such as aluminum acetate, ceruminolytics such as sodium chloride solution, hydrogen peroxide or sodium bicarbonate solution. The solutions may be administered to one ear or both ears (unilaterally or bilaterally) and the solutions may be administered sequentially or simultaneously.

In order to ensure that the ear canal is completely filled with the drug solution, the ear canal may be initially filled manually with the therapeutic solution. Such filling of the ear canal may be done through the use of the manual fill nozzle shown in FIGS. 7A and 7B and described further below. To ensure that the ear canal is completely filled and that there are no air pockets remaining, the patient's head may be tilted to one side, the ear canal filled using the manual fill nozzle, and then the ear canal is sealed using the appropriate headset 200 and ear plug 304 combination compatible with the size and shape of the patient's head and the size and shape of the patient's ear canal, as will be described further below.

Figure 3A:
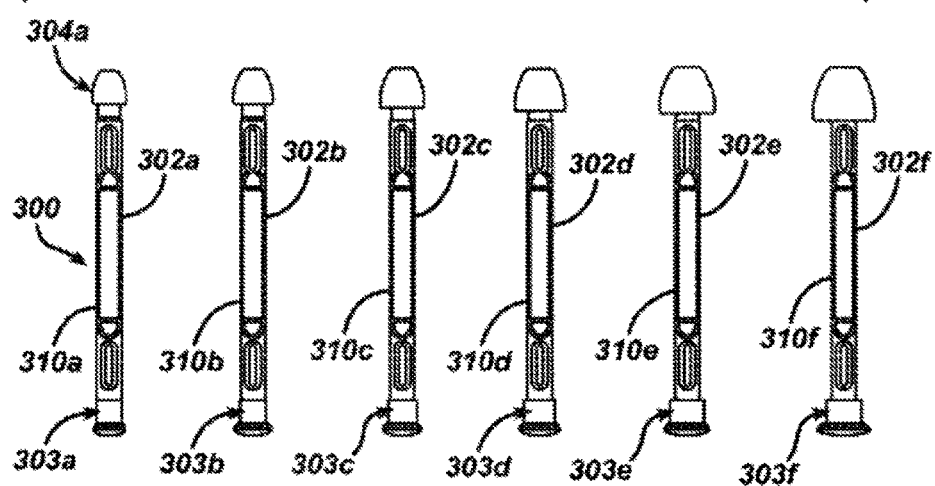
FIG. 3A shows a perspective view of a set of ear plug sizers according to one embodiment of the invention.
Figure 3B:
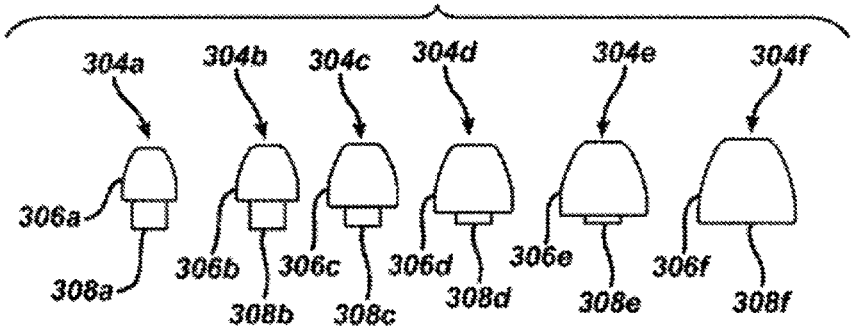
FIG. 3B shows a perspective view of a set of ear plugs for iontophoretic substance delivery according to one embodiment of the invention.
Figure 3C:
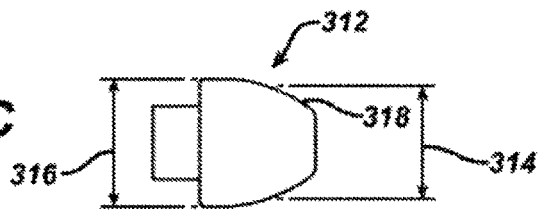
FIG. 3C shows a side view of an ear plug for iontophoretic substance delivery according to one embodiment of the invention.

Once the appropriate headset 200 has been chosen, the appropriate ear plugs may be chosen such that the plugs can be attached to the headset and can provide a seal to keep anesthetizing solution or other therapeutic solution in the ear canal 118. As shown in FIG. 3A, a set 300 of ear plug sizers 302a, 302b, 302c, 302d, 302e and 302f may be provided that will aid in determining which size will best fit the patient's anatomy. The ear plug sizers 302a-f are provided with lugs 303a-f and ear plugs 304a-f. In the illustrative embodiment, there are 6 different ear plug sizes, but in other embodiments there may be 1, 2, 3, 4, 5, 7, 8 or even more than 8 ear plug sizes. The lugs 303a-f are constructed for example of a rigid plastic material for insertion past the concha 104 (see FIG. 1A) and into the ear canal (118) for initial selection of the size of the ear plugs 304a-f. The outer diameters of the lugs are equivalent to the sealing diameters of the ear plugs. The ear plugs 304a-f are further shown in FIG. 3B. Each ear plug 304a-f is made of a flexible material that can conform to the contours of the ear canal and may be made of silicone rubber or other similar materials such as polyurethane, styrene butadiene, butyl, and fluorosilicone rubbers. Each ear plug 304a-f is constructed of a rounded distal end 306a-f for insertion into the ear canal 118 and orientation toward the tympanic membrane 122 (see FIG. 1B) and a tubular proximal end 308a-f for attachment to the ear plug sizer 302a-f (See FIG. 3A) or for attachment to the headset 200 over electrodes 210a and/or 210b. As shown in FIG. 3C an exemplary umbrella shaped ear plug 312 has a sealing diameter (SD) 314 that fits against the ear canal for sealing the iontophoresis solution into the ear canal and a maximum outer diameter (OD) 316 contains one to ten vent holes 318 with diameters between 0.001 and 0.050 inches that enable air and excess fluid to escape during iontophoresis solution delivery.

In one embodiment, the ear plugs sizers 302a-f are provided as a set of six (6) color-coded parts and correspond to six (6) color-coded ear plug 304a-f sizes. Size 0 (the smallest) is purple (SD=0.276", OD=0.323") , Size 1 is orange (SD=0.315", OD=0.364"), Size 2 is green (SD=0.354", OD=0.408"), Size 3 is yellow (SD=0.394", OD=0.452"), Size 4 is red (SD=0.433", OD=0.497") and Size 5 is green (SD=0.472", OD=0.548"). The shafts 310a-f of the ear plug sizers 302a-f are color-coded, rigid and attached to the ear plugs 304a-f, so that a health care professional can hold one of the ear plug sizers 302a-f and insert it into the ear canal of the patient prior to treatment to determine the appropriate size useful for the particular anatomy of the patient. The ear plug sizer that is believed to best match the opening of the ear canal should be used, and the health care professional should try one size larger and one size smaller to confirm the appropriate size. Once the proper ear plug is determined, it is placed over the locking arm elbow of the headset 200. The lumen of the tubular portion of the selected ear plug is pushed over the fill system tip 224a or 224b of the headset arm 208a or 208b until it seats into place against the lips 222a and 222b of the locking arm elbows 212a and 212b. The fill system tips 224a and 224b of the headset have three spray holes in an atraumatic tip for easy filling of the ear canal 118 through the fluid delivery channels 226a or 226b attached to the fill system valves 214a and 214b. The spray holes and atraumatic tip portion of the fill system tips 224a and 224b are similar to the spray holes 806 and atraumatic tip 808 of the manual fill nozzle 800 described below with regard to FIGS. 7A and 7B. In addition, a design of the fill system tips 224a and 224b more similar in shape to the ear canal 118 may be useful. The most distal portion of the fill system tip 224a and 224b should be near the tympanic membrane such that the spray holes face the tympanic membrane. Accordingly, the fill system tips 224a and 224b may essentially span the distance from the locking elbows 212a and 212b to the tympanic membrane. The number of spray holes range from one to three or more and are evenly distributed one from the other (where there are three spray holes, they are spaced 120 degrees apart) to create turbulence in the ear canal 118. Further, the most distal portion of the fill system tip 224a or 224b is designed to face the tympanic membrane 122 such that during iontophoresis, the ear canal fills from the portions closest to the tympanic membrane out towards the outer ear 10 and air that has accumulated in the ear canal 118 will be evacuated as a result of low pressure escape of air through vent holes 318 in the ear plugs 312 as shown in FIG. 3C. In this way, air bubbles in the ear canal are minimized, leakage of therapeutic solution from the ear canal is minimized and pressure in the ear canal is maintained at below about 50 kilopascals and often below about 25 kilopascals.

The electrodes 210a and 210b consist of a solid silver electrode with a cylindrical shape attached to the electrode wiring 218 (see FIG. 2). Small openings in the fluid delivery channels 226a and 226b near the electrodes 210a and 210b ensure that the electrodes are submerged in and establish electrical connection with the anesthetizing solution and the system operates properly. During the iontophoresis procedure, the electrode conductivity changes due to electrochemical reactions between the electrode and the anesthetizing solution. This change may raise the voltage from the iontophoresis system. An electrode with greater surface area may be desirable. In one embodiment, the electrode may be made of a single wound coil and in another embodiment, it may be made of two concentric-oppositely wound coils of silver wire may be provided with a gap between the inner surface of the outer coil and the outer surface of the inner coil. The inner coil may have an open space on the inner diameter. The outer coil may be right hand wound and the inner coil may left hand wound, or alternatively, the outer coil may be left hand wound and the inner coil may be right hand wound. In another embodiment, the coil wire may be formed against the inside wall of the ear plug lumen and integrated into the ear plug to provide maximum surface area and maximum space between electrode elements. The anesthetizing solution flowing in around the lumen will encounter little interference and therefore will submerge the electrode efficiently, ensuring good contact with the electrode. The electrode material can be silver, gold, platinum, silver-silver chloride, stainless steel or any other materials that can achieve the electrochemical function of the electrode.

Figure 4:
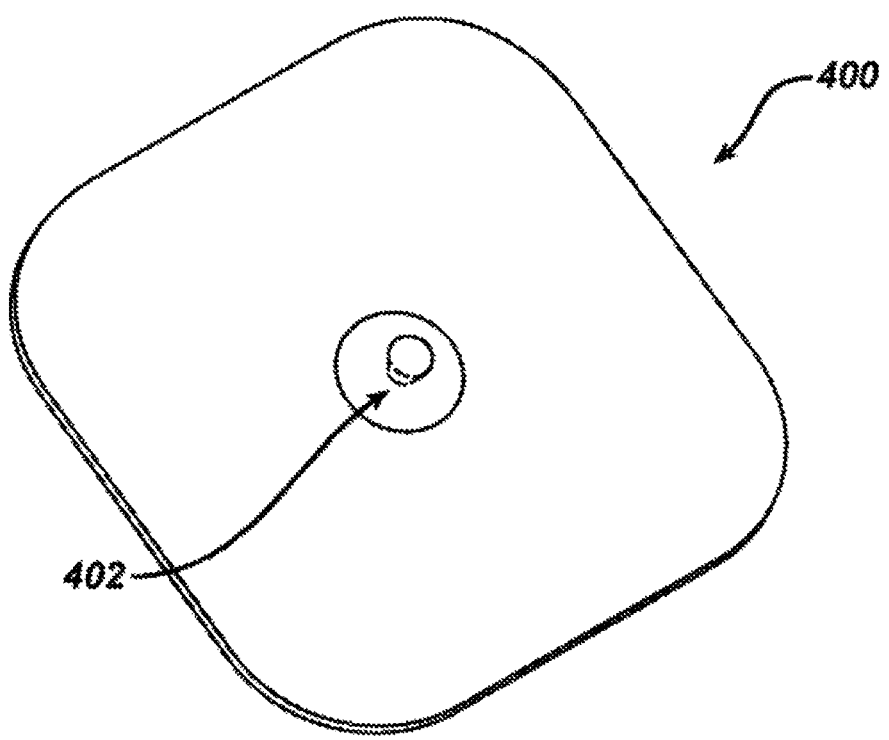
FIG. 4 shows a perspective view of a return electrode patch for iontophoretic substance delivery according to one embodiment of the invention.

Once the appropriate ear plug 304 has been placed on the appropriate headset 200, return electrode patch 400 is attached to the headset at the return electrode connector 220 by connection at the mechanically conductive return electrode snap 402. The return electrode patch 400 is shown in FIG. 4 and may be adhered to the patient's skin at a clean, dry site, such as the arm or back, that is clear of lesions, bony protuberances, and excessive hair. A protective lining may be supplied on the base of the patch 400, such that when the lining is removed, an adhesive layer on the patch 400 may be adhered to the skin.

Figure 5:
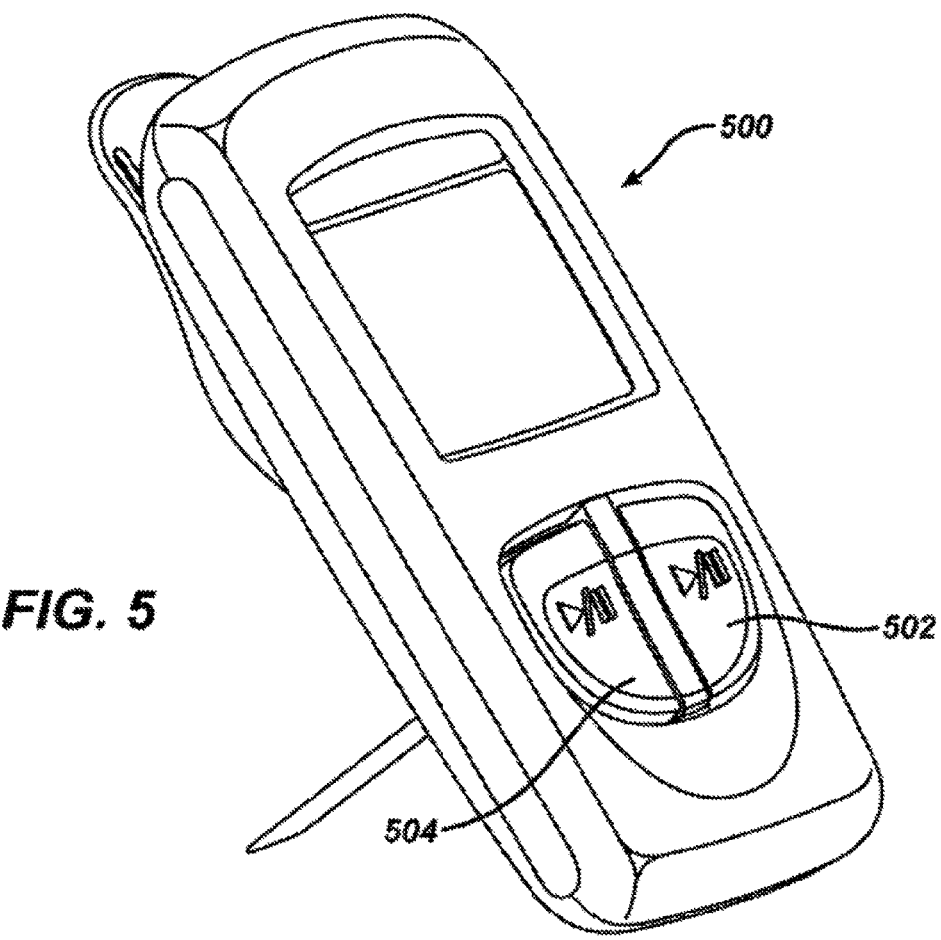
FIG. 5 shows a perspective view of a control unit for iontophoretic substance delivery according to one embodiment of the invention.

Following positioning of the headset 200 on the patient's head and the return electrode patch 400 on the patient's skin as will be described below, the control unit 500 shown in FIG. 5 may be connected to the control unit connector 220 on headset 200 as shown in FIG. 2 and the headset 200 will be clipped to the patient's or the parent's clothing.

Figure 6:
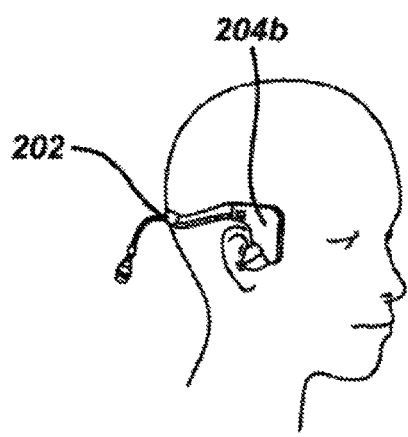
FIG. 6 shows a perspective view of the proper positioning of the headset on a patient's head.
Figure 7A:
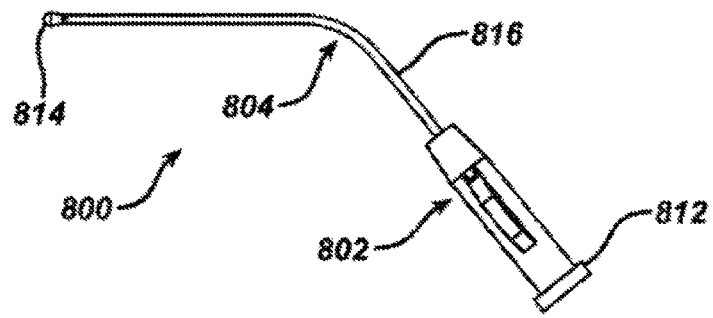
FIG. 7A shows a perspective view of a manual fill nozzle according to one embodiment of the invention.
Figure 7B:
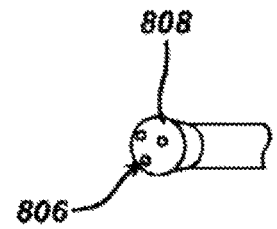
FIG. 7B shows a perspective view of the nozzle tip of the manual fill nozzle of FIG. 7A.
Figure 8:
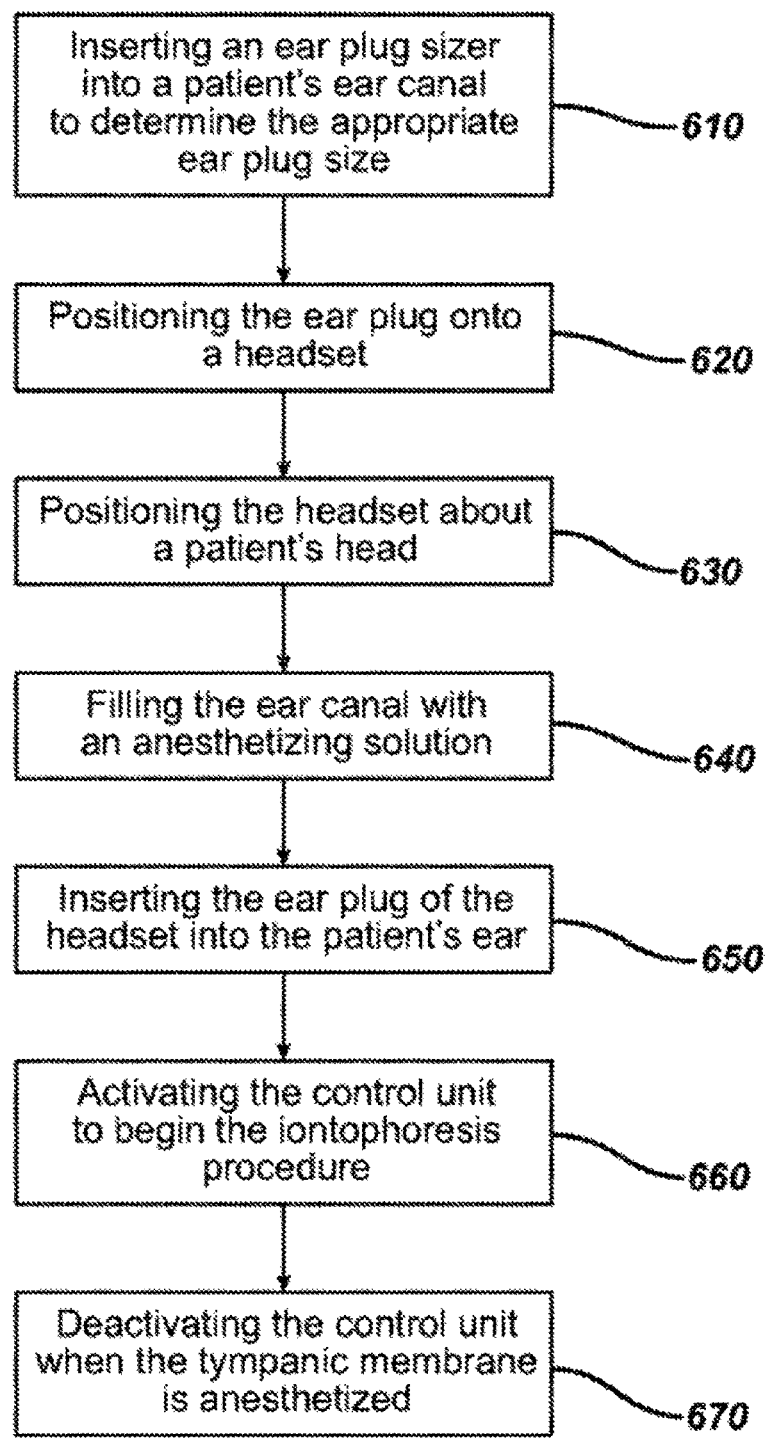
FIG. 8 is a flow diagram showing the method of the invention for anesthetizing the ear canal.

The method according to the invention is carried out according to FIG. 8. The anesthetizing solution is prepared (in this case a solution of 1:12,000 epinephrine, 3.3% lidocaine and 0.7% sodium bicarbonate but may be any appropriate combination thereof such as lidocaine, lidocaine plus epinephrine, or lidocaine plus epinephrine and sodium bicarbonate or other anesthetizing solution known in the art) and warmed to body temperature. A syringe is filled with approximately 10 cc of anesthetizing solution. The headset 200 is prepared for placement on the patient as follows. As previously described above with regard to FIGS. 3A, 3B and 3C, an ear plug sizer is placed into a patient's ear canal to determine the appropriate ear plug size for personalization of the headset according to the size and shape of the patient's ear canal (610). The appropriate ear plug is positioned onto the headset (620). The spring loaded locking arms 208a and 208b are opened and locked by rotating them outwards until they click and until they hold a position pointing in the outward direction. While being held at the site of the temporal pads 204a and 204b, the headset 200 is carefully placed about the patient's head (630) such that the temporal cushions 206a and 206b are resting on the patient's temporal bone and the headset frame 202 is routed around the back of the patient's head (see FIG. 6). The return electrode patch 400 is connected to the headset 200 via the return electrode snap 402 on the electrode patch 400 and the return electrode connector 216 on the headset 200 and the adhered to the patient. The integrated fill system of the headset is primed with the anesthetizing solution by attaching the syringe to the fill system valves 214*a* and 214*b* and injecting until the solution exits the ear plug 312. The syringe is disconnected and reconnected to the other side if both ears are being treated. The syringe is then connected to the manual fill nozzle 800 (See FIGS. 7A and 7B).

Once the headset 200 is properly primed and positioned, the auricle 100 of the ear is gently pulled to straighten the ear canal 118. Using the syringe with the manual fill nozzle 800 attached at the luer connector 802, the ear canal 118 is manually filled with anesthetizing solution (640), taking care to eliminate air bubble formation during the fill (see FIGS. 7A and 7B). The manual fill nozzle 800 has a proximal end 812, a distal end 814 and a lumen 816 therebetween that may have a bend angle 804 of 130 degrees (or between about 120 degrees and 140 degrees, or it may have an angle of between 0 and 140 degrees to enable microscopic visualization of the ear canal while the solution is administered) and 3 spray holes 806 in an atraumatic tip 808 for easy filling of the ear canal 118 under direct visualization. A typical ear canal 118 will accommodate approximately 1-2 cc of fluid. The anesthetizing solution is administered via the manual fill nozzle 800 at a flow rate of approximately 0.5 cc/sec and is overfilled to ensure that all air has been evacuated. The three spray holes distributed 120 degrees apart on the tip provide for solution turbulence when filling the ear canal. There may be any number of spray holes between 3 and 12, for example 4, 5, 6 or more spray holes that are distributed about the atraumatic tip 808 of the manual fill nozzle 800. After the anesthetizing solution has been administered to the ear canal, while holding the auricle 100 with one hand, the other hand may be used to unlock the locking arms 212*a* and 212*b* of the headset 200 and insert the ear plug 312 into the ear canal so that the tip of the ear plug 312 points towards the tympanic membrane (650). In addition, the locking and unlocking of the locking arms 212*a* and 212*b* may be carried out at any time during the filling ear canal and iontophoretic delivery of the solution in order to visually observe the ear canal.

The headset control unit connector 220 is connected to the control unit 500 until it snaps in place. The battery tab located on the back of the control unit case is removed. Empty status bars should appear on screen once the device is powered on. To start the iontophoresis procedure, the control unit is activated (660) by pressing the yellow button 502 and/or the blue button 504 on the control unit 500 are holding for 2 seconds. Each button controls an independent channel, with button colors corresponding to the colors of the left and right sides of the headset. A short beep confirms when a button has been activated. The control unit 500 is clipped to the patient's or the parent's clothing. The status bars will fill up to indicate each channel's progress toward completion. A typical procedure takes approximately 10 minutes, with each status bar segment representing approximately 20% of procedure time. A flashing segment indicates that current is running; a solid segment indicates the portion already completed. To pause the procedure, the button for the appropriate channel is pressed and held for 2 seconds. The pause symbol and status bar segment will both flash and then turn solid when current delivery has stopped. To resume the procedure, the same button is pressed and held for 2 seconds. The control unit 500 will play a long beep when each channel (yellow or blue side) has completed delivering a full dose. The status bars will also turn completely solid to indicate that full charge has been delivered through each channel. Once the tympanic membrane is anesthetized, to deactivate the control unit, the button for the appropriate channel is pressed and held for 2 seconds (670). Alternatively, the control unit may stop after a preset period of time of between about 5 minutes and 60 minutes, often between about 5 minutes and 30 minutes or about 10 minutes.

The procedure described above may also be useful for administering a therapeutic solution to the ear canal without the use of iontophoresis. The headset may be placed on the head of the patient and the ear may be primed with the therapeutic solution as described above followed by placement of the ear plugs into the ears, or the ear plugs may be inserted into the ears and the therapeutic solution administered through the headset fill system valves 214*a* and 214*b*. One or both of the valves (in this case, one way valves) are connected to delivery devices such as syringes or delivery pumps and the therapeutic solution is administered to one or both ear canals (unilaterally or bilaterally) either sequentially or simultaneously. As noted above, vent holes 318 are incorporated in the ear plugs to ensure that the ear canal is not over filled and thereby cause pressure to build up in the ear canal. Other vent systems for ensuring proper venting to ensure that patient comfort is maintained include but are not limited to vent slits and vent screens.

Proper sizing of the headset and the ear plugs ensure proper filling of the ear canal and further aid in retaining the therapeutic solution in the ear canal for a predetermined period of time that coincides with the duration of therapy. Such period of time may be from about five to ten minutes to about one to two hours. The therapeutic solution may be removed from the ear canal following the therapy by positioning of the patient's head, suctioning of the ear canal, or other procedures including but not limited to tympanocentesis.

Figure 7C:
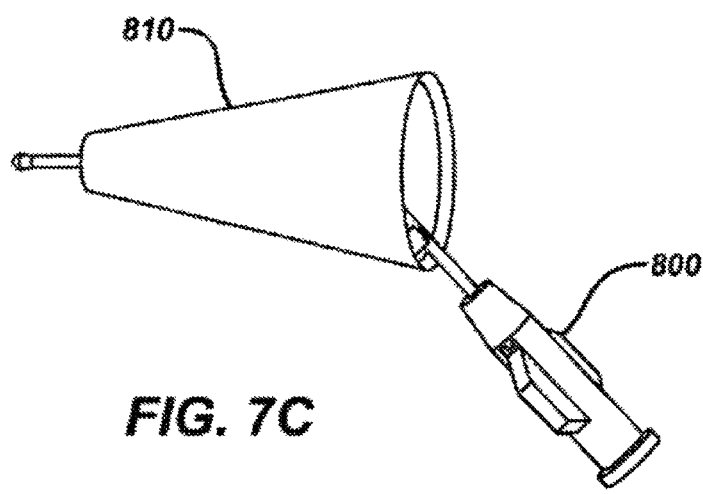
FIG. 7C shows a perspective view of the manual fill nozzle of FIG. 7A in combination with a speculum according to a further embodiment of the invention.

In an alternative aspect of the invention, the manual fill nozzle 800 shown in FIG. 7A and FIG. 7B may be incorporated into a rigid speculum 810 and fixedly attached thereto as shown in FIG. 7C for easy and accurate insertion of the nozzle 800 by the physician user allowing direct visualization of the outer ear and the tympanic membrane. Further, the manual fill nozzle may be used for purposes other than administration of iontophoresis solution. It may be used for anesthetizing the ear canal or tympanic membrane or for administering solutions for other therapeutic purposes. Such solutions include but are not limited to antifungal or antibacterial agents such as benzalkonium chloride, boric acid, acetic acid, and clotrimazole, anti-inflammatory agents such as beclamethazone and antibiotic and steroids such as betnesol, prednisolone sodium phosphate, gentamycin, neomycin, and quinolones, astringent agents such as aluminum acetate, ceruminolytics such as sodium chloride solution, hydrogen peroxide or sodium bicarbonate solution.

Figure 9:
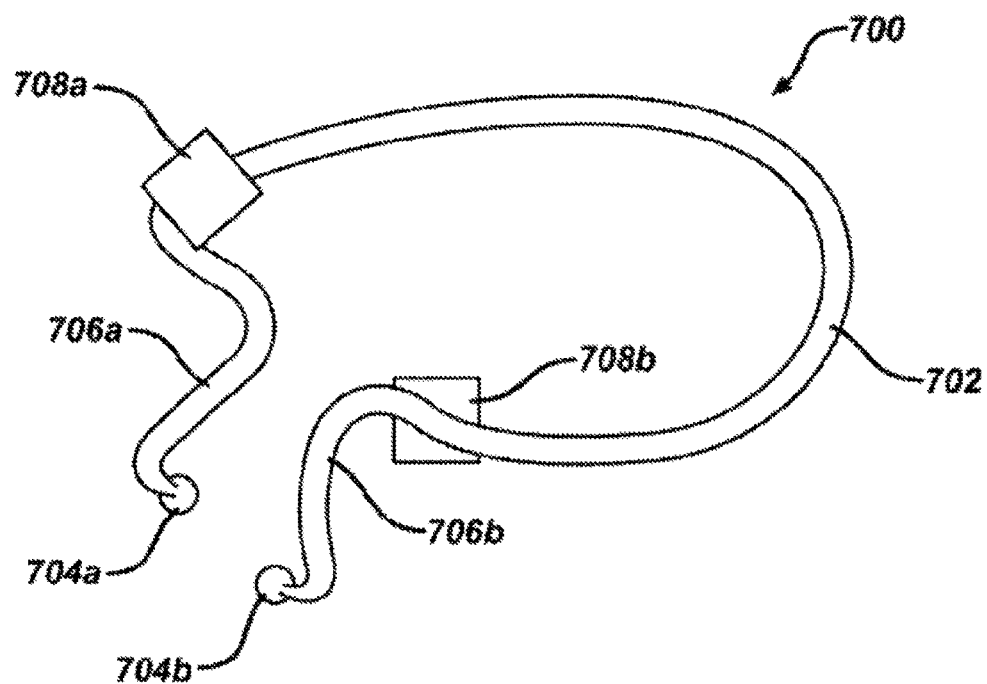
FIG. 9 is a perspective view of a headset for iontophoretic drug delivery according to the invention.

An alternative headset 700 is shown in FIG. 9. In this embodiment, a wire support frame 702 is provided to minimize hand to auricle contact by the healthcare professional, reduce the time to insert the ear plugs 704*a* and 704*b* into the ear canals, and provide support to the ear plug in the x, y and z axis. A wire frame 706*a* and 706*b* for around each ear is provided to support the ear plug in the x and y directions and a pad 708*a* and 708*b* for each ear, in this case of white foam Y20 cross-linked closed cell 2 pound density but may be other similar material, is provided to support the ear plug in the z direction. In this embodiment, and in the embodiments described above, the headset and fill systems are designed for maximum patient comfort and stability. The headsets are designed such that the pressure of the device is distributed about the patient's head and not solely in or on the ears. The fill system tubing is routed (and iontophoresis system wiring, if included) outside of the treatment area, such as behind the patient's head and may be secured behind the patient's neck with a system connector such as a tie, clip or other similar connector.

As noted above, according to the method of the invention, it is important to ensure that air bubbles in the anesthetizing solution or therapeutic solution are minimized Air bubbles may result from a variety of conditions including but not limited to orientation of the canal relative to gravity, surface tension of the liquid and surface conditions of the canal, such as a waxy ear canal wall. An alternative system is described for evacuating the external ear canal prior to filling such that minimal air bubbles are left behind in the anesthetizing solution. To enable reliable and tolerable filling of an ear canal in an awake patient, evacuation of entrapped air bubbles may be accomplished by providing a dual chamber instillation device. A first chamber of double or triple the volume of the liquid required to fill the canal is provided. This first chamber has a plunger or other means to forcibly expel liquid out and through an instillation port. A second chamber, vented to atmosphere, captures and stores excess liquid returning from the outlet port. Ear plugs with instillation and outlet ports are hydraulically balanced to enable filling of the ear canal with low pressure (supplied through the Instillation Chamber). Balancing is achieved by orifice diameter selection. The instillation port is constructed to create a turbulent flow at low exit pressure such that an irrigation effect is achieved, maximum surface wetting is obtained with minimum flow rate, and mobility of air bubbles is maximized. The slight positive pressure created within the ear canal mobilizes any air bubbles such that they will travel out of the outlet port. Low exit pressure is required to minimize the likelihood of pain due to high pressure jetting of liquid against sensitive tissue of the ear canal wall or tympanic membrane. Embodiments of the instillation port include tubing with a fine mesh screen to create separation and reduce fluid head, and alternatively, providing a tube with a coaxial, protracting structure to divert and separate flow.

In operation, the instillation chamber is filled with a volume greater than the volume of the ear canal. Ear plugs are inserted into the ear canal. The patient's ear canal is oriented vertically to reduce the likelihood of bubble entrapment. The plunger is driven to completely expel all liquid from the instillation chamber. The instillation device is disconnected from the plug and a fluid seal is maintained with bubbles evacuated.

Air in the fluid delivery channel and inside the electrode must be removed with low fluid pressure in order to minimize dead-space that would insulate the working electrode from the fluid and therefore increase system impedance. A method to manage air entrapment during application and use of anesthesia fluid is further described herein. Semi-porous material such as expanded polytetrafluoroethylene (EPTFE) or sintered solid EPTFE may be incorporated directly into the electrode housing or inside the ear canal interface of the device. The air in the fluid delivery channel and inside the electrode housing may be removed with low anesthetizing solution pressure since the required fluid pressure is inversely proportional to the porosity of the material used. To further remove entrapped air such as microbubbles in the system, a surfactant may be added to the anesthetizing solution to assist wetting and effectively decrease the surface tension of the incoming liquid to prevent formation of the bubble. Such surfactants may be any commonly used surfactant such as polyethylene glycol. During system filling, this would allow for dislodgement, coalescence and escape of microbubbles from the system through the semi-porous material. Other alternatives to remove entrapped air include a fluid-activated valve that would allow air to escape but would seal itself upon fluid entry, a one-way air valve incorporated in vent holes that would allow air and fluid to overflow but prevent any fluid from re-entering the system, an air reservoir in the system that would allow entrapped air to accumulate but strategically located not to disrupt anesthetizing solution delivery, or reducing surface tension by cleaning or etching the parts or enhancing their surface finishes such that microbubble formation is reduced.

Minimizing surface area on the inside of the ear plugs to prevent air bubbles from sticking to the inside surface of the ear ply and travelling into the elbow, blocking the conductance of the electrode is accomplished by providing 4 slots equally spaced at 90 degrees apart starting on the outside surface of the ear plug and travelling around to the inside diameter on the distal end of the ear plug. Flat surface are inside the ear plug creates tension between the air bubble and the earplug with allow the air bubbles to block electrode conductance. Slotted surface are minimized tension between air bubbles and the plug preventing such blockage.

Fluid leakage around the earplugs leads to air pockets in the ear canal that disrupt iontophoresis. With a constant pressure system, when fluid leaves the ear, it is immediately replaced, reducing air pocket development and further reducing user variability in delivering the fluid and the possibility of insufficient fluid in the ear canal. In an alternative embodiment of the invention, a compressed air canister is preloaded with a desired pressure. This air pressure is allowed to press against a piston, thereby delivering anesthetizing solution at a desired pressure. In an alternative embodiment, an expanding polymer such as polyacrylic acid can be used to created pressure, thereby propelling the anesthetizing solution once the polymer is wetted. Further embodiments would involve the use of a spring or rubber band to propel the anesthetizing solution or the use of a weight to press down on the anesthetizing solution with a constant gravitational force. Yet another embodiment would contemplate the acceleration of anesthetizing solution using an electrical charge to deliver precise pressure levels for delivery of the anesthetizing solution.

The invention has been described with reference to certain examples or embodiments of the invention, but various additions, deletions, alterations and modifications may be made to those examples and embodiments without departing from the intended spirit and scope of the invention. For example, any element or attribute of one embodiment or example may be incorporated into or used with another embodiment or example, unless otherwise specified or if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

The invention claimed is:

1. A system for administering a solution to a tympanic membrane of an ear canal of a subject, the system comprising:
a fluid delivery channel with a proximal end, a distal end, and a lumen defined therebetween, the proximal end configured for selectively establishing fluid communication between a solution source and the lumen of the fluid delivery channel, the distal end including an atraumatic tip defining a plurality of spray holes for providing fluid communication between the lumen and the ear canal, the atraumatic tip having an outer diameter greater than an outer diameter of a portion of the fluid delivery channel proximal of the atraumatic tip, the atraumatic tip capable of being inserted into the ear canal and positioned near the tympanic membrane with the plurality of spray holes substantially facing the tympanic membrane to fill the ear canal with the solution from a portion near the tympanic membrane out toward an outer ear portion; and an ear plug capable of conforming to at least one of a size and a shape of the ear canal to reduce leakage of the solution from the ear canal at least one of during and following administration of the solution, the ear plug including a vent system via which accumulated air from a portion of the ear canal distal to the ear plug can be evacuated through the ear plug to a portion of the ear canal proximal to the ear plug.

2. A system for administering a solution to a tympanic membrane of an ear canal of a subject, the system comprising:

an ear plug capable of conforming to at least one of a size and a shape of the ear canal to reduce leakage of the solution from the ear canal at least one of during and following administration of the solution, the ear plug including a vent system via which accumulated air from a portion of the ear canal distal to the ear plug can be evacuated through the ear plug to a portion of the ear canal proximal to the ear plug; and a fluid delivery channel with a proximal end, a distal end, and a lumen defined therebetween, the proximal end configured for selectively establishing fluid communication between a solution source and the lumen of the fluid delivery channel, the distal end including an atraumatic tip defining a plurality of spray holes for providing fluid communication between the lumen and the ear canal, the atraumatic tip capable of being inserted into the ear canal and disposable distal to the ear plug such that the atraumatic tip can be positioned near the tympanic membrane with the plurality of spray holes substantially facing the tympanic membrane to fill the ear canal with the solution from a portion near the tympanic membrane out toward an outer ear portion.

3. The system of claim 2, wherein the plurality of spray holes includes three to twelve spray holes.

4. The system of claim 2, wherein the plurality of spray holes are evenly distributed on the atraumatic tip.

5. The system of claim 4, wherein the plurality of spray holes includes three spray holes spaced 120 degrees apart.

6. The system of claim 2, wherein the solution is at least one of an anesthetizing solution, an antibacterial solution, an antifungal solution, an anti-inflammatory solution, or a ceruminolytic solution.

7. The system of claim 6, wherein the anesthetizing solution includes at least one of lidocaine, epinephrine, or sodium bicarbonate.

8. The system of claim 2, wherein the vent system includes at least one of a vent hole, a vent slit, or a vent screen.

9. The system of claim 2, wherein the vent system includes a one-way air valve.

10. The system of claim 2, wherein the vent system is configured to maintain a maximum pressure in the ear canal of about 50 kilopascals or less.

11. The system of claim 10, wherein the vent system is configured to maintain the maximum pressure in the ear canal at about 25 kilopascals or less.

12. The system of claim 2, further comprising an iontophoresis electrode operably connected to a control unit and a return electrode.

13. The system of claim 2, further comprising a speculum capable of providing direct visualization of the tympanic membrane.

14. The system of claim 2, further comprising a headset including a headset frame capable of conforming to at least one of a size or a shape of a head of the subject.

15. The system of claim 2, wherein the atraumatic tip has an outer diameter greater than an outer diameter of a portion of the fluid delivery channel proximal of the atraumatic tip.

16. A method for administering a solution to a tympanic membrane in an ear canal of a subject, the method comprising:

introducing a distal end of a fluid delivery channel into the ear canal, the fluid delivery channel having a proximal end and a lumen defined between the proximal end and the distal end, the proximal end configured for selectively establishing fluid communication between a solution source and the lumen of the fluid delivery channel, the distal end including an atraumatic tip defining a plurality of spray holes;

positioning (i) an ear plug within the ear canal such that the ear plug conforms to at least one of a size and a shape of the ear canal and (ii) the atraumatic tip within the ear canal distal to the ear plug such that the atraumatic tip can be positioned near the tympanic membrane with the plurality of spray holes substantially facing the tympanic membrane;

filling the ear canal with the solution from a portion near the tympanic membrane out toward an outer ear portion by providing fluid communication between the solution source and the lumen of the fluid delivery channel, via the proximal end of the fluid delivery channel, and between the lumen of the fluid delivery channel and the ear canal, via the plurality of spray holes, the ear plug reducing leakage of the solution from the ear canal at least one of during and following the filling of the ear canal; and evacuating accumulated air, using a vent system of the ear plug, from a portion of the ear canal distal to the ear plug through the ear plug to a portion of the ear canal proximal to the ear plug.

17. The method of claim 16, further comprising:
establishing an electrical connection between an iontophoresis electrode and the solution via a control unit connected to the iontophoresis electrode and a return electrode attached to the subject.

* * * * *